United States Patent [19]

Cumer et al.

[11] Patent Number: 5,665,069

[45] Date of Patent: Sep. 9, 1997

[54] PRESSURE-DIRECTED PERIBULBAR ANESTHESIA DELIVERY DEVICE

[76] Inventors: Patricia Lynn Cumer, 1017 Pioneer Cir., Argyle, Tex. 76226; Peter Ivan Rivera, 2184 Buckingham Rd., #407, Richardson, Tex. 75081

[21] Appl. No.: 684,548

[22] Filed: Jul. 19, 1996

[51] Int. Cl.⁶ .................................................. A61M 5/00
[52] U.S. Cl. .................. 604/116; 604/174; 604/177; 604/300
[58] Field of Search .................... 604/115, 116, 604/117, 174, 177, 300, 301, 302; 206/363, 364, 365

[56] References Cited

U.S. PATENT DOCUMENTS

| | | | |
|---|---|---|---|
| 4,639,248 | 1/1987 | Schweblin | 604/187 |
| 4,664,128 | 5/1987 | Lee | 604/187 |
| 5,009,643 | 4/1991 | Reich et al. | 604/165 |
| 5,092,837 | 3/1992 | Ritch et al. | 604/294 |
| 5,098,389 | 3/1992 | Cappucci | 604/158 |
| 5,338,309 | 8/1994 | Imbert | 604/187 |

FOREIGN PATENT DOCUMENTS

| | | |
|---|---|---|
| 432363A2 | 6/1991 | Germany . |
| WO9305833 | 4/1993 | WIPO . |

*Primary Examiner*—Sam Rimell
*Assistant Examiner*—Robert V. Racunas

[57] ABSTRACT

A device useful in the injection of an anesthetic into the peribulbar region of the eye. The device includes a needle assembly functionally integrated with a flange shaped to provide pressure to the desired region. The device in combination with a syringe and needle allows the injection of anesthetic under pressure and directed toward the peribulbar region of the eye, adequately distributing the anesthetic throughout the peribulbar space more efficiently.

2 Claims, 4 Drawing Sheets

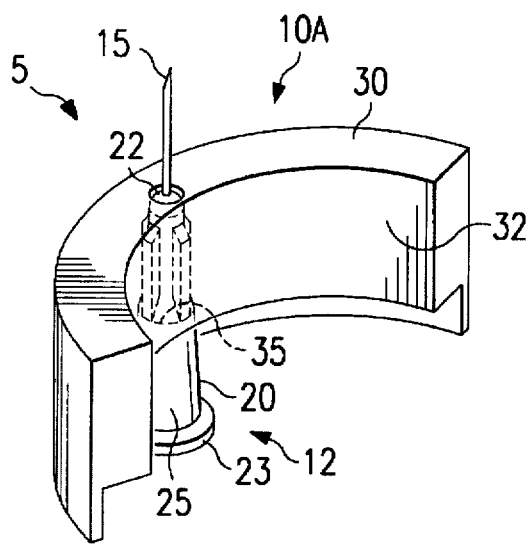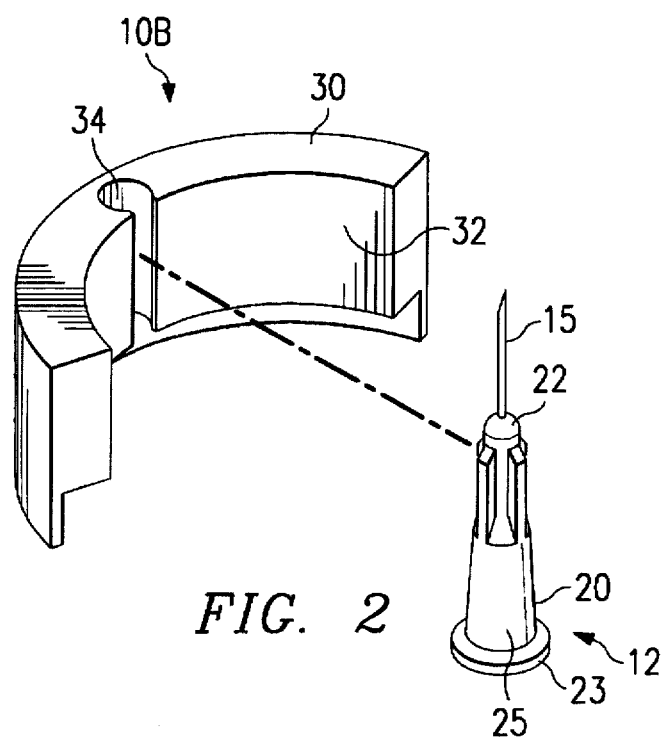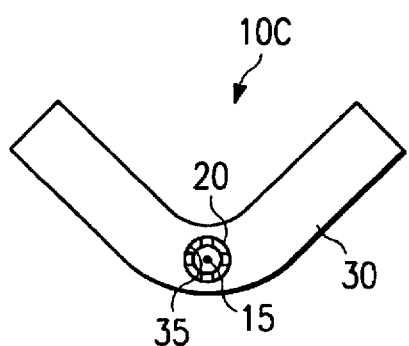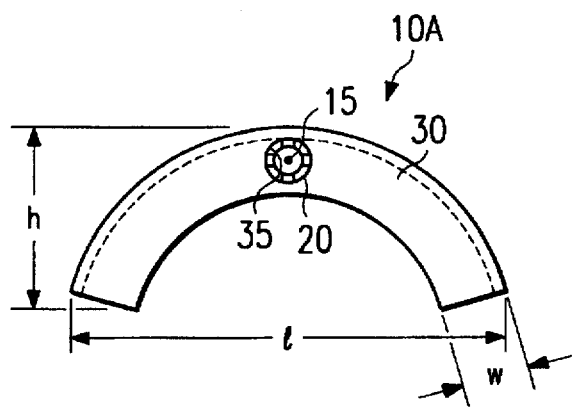

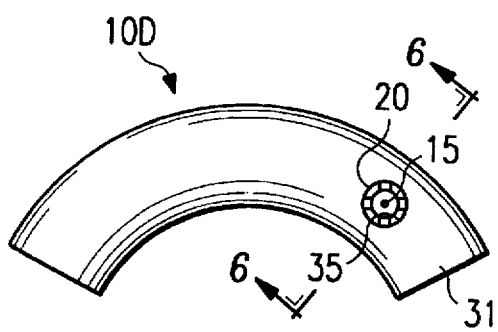
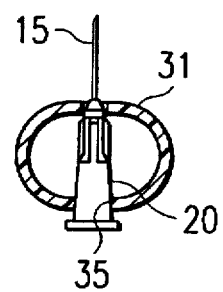
FIG. 5    FIG. 6
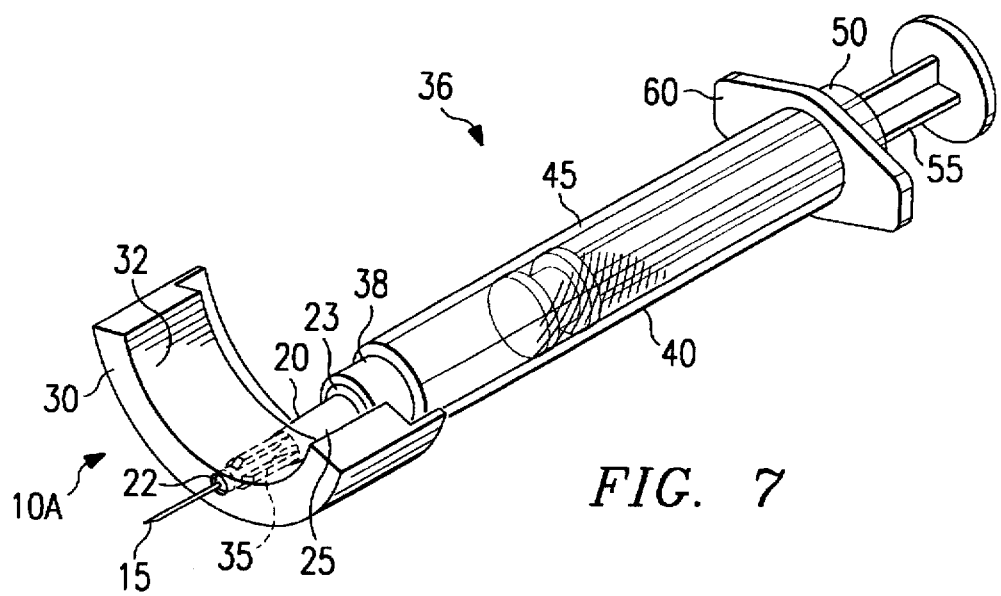
FIG. 7
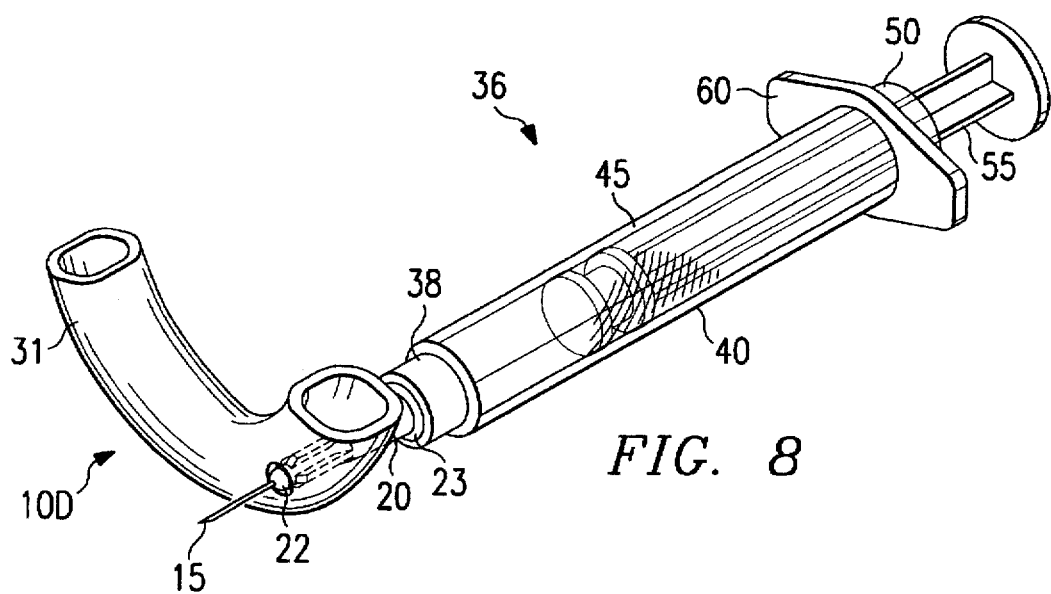
FIG. 8

5,665,069

PRESSURE-DIRECTED PERIBULBAR ANESTHESIA DELIVERY DEVICE

TECHNICAL FIELD OF THE INVENTION

This invention relates to the field of medical syringes and needles, in particular, those for administering anesthesia before eye surgery.

BACKGROUND OF THE INVENTION

The majority of ophthalmic surgery is now done under local anesthesia, most of which is administered by peribulbar or retrobulbar injection. The three main objectives of a peribulbar anesthetic block are: loss of pain sensory function, loss of motor function, and globe softness. A failure to obtain a satisfactory anesthetic block, therefore, will result in pain and discomfort to the patient and a more difficult labor for the surgeon. In actual practice, when the practitioner has an assistant at hand to assist with the anesthetic, the block success rate at meeting the above objectives may be improved by the judicious application of digital pressure to the lower lid at the injection site. This action prevents the anesthetic from spreading throughout the lower lid tissue, instead directing it rearward, into the peribulbar space, where the desired effects are obtained. In most practice settings, the luxury of having an assistant who is experienced at this technique is not available. To attempt this maneuver with just two hands is to sacrifice the needle stability in the hand of the operator. This would increase the risk of globe perforation, hemorrhage, and other possible complications known to occur with this type of anesthesia.

Current practice in retrobulbar anesthesia involves the use of a 1½ inch needle and typical anesthetic volumes of about 3–5 cc. Peribulbar anesthesia typically involves the use of a 1 inch needle with volumes of 6–10 cc. The longer needle used in retrobulbar anesthesia increases the risks of retrobulbar hemorrhage and nerve injury since the intraorbital neurovascular structures tend to become less mobile the further back into the orbit they are located. The shorter needle of the peribulbar method of anesthetic block is favored in this respect; however, the disadvantage with it is the higher volume of anesthetic required and the lower success rate since the effectiveness of the block is directly dependent upon the favorable spread of the anesthetic. The higher volume of anesthetic increases the chances of forward diffusion of the anesthetic, leading to swelling of the conjunctiva which interferes with the surgical field, making the operation more difficult.

A new device is herein disclosed which alleviates the awkwardness and difficulty of administering the local anesthetic into the peribulbar area of the eye and, assures the proper distribution of the anesthetic throughout the peribulbar space. The device is especially useful when the administrator of the block has no assistance available. The invention has the additional advantage of reducing the amount of anesthesia necessary. A peribulbar block can be done effectively with the disclosed device using a lower dose previously only used in increased risk retrobulbar anesthesia procedures. Moreover, it is possible to effectively use a shorter needle with the present invention, thereby increasing safety to the patient.

SUMMARY OF THE INVENTION

In one aspect the present invention relates to a pressure-directed flange attached to a standard hypodermic needle's hub. The flange is dimensioned to be pressed adjacent the under-eye skin surface in use, in the region adjacent the inferior orbital ridge. The flange has a portion defining a tunnel, said portion dimensioned to receive a hub of a hypodermic needle so that said hub is held substantially perpendicular to the flange, said needle extends outwardly from a first body-contacting side of said flange and said hub extends sufficiently outwardly from said second side of said flange so that it is able to receive the connector of a standard syringe barrel.

Another aspect of the present invention relates to a pressure-directed flange having an integral hub. The flange is dimensioned such that in use, it applies pressure to both the sides of the needle outwardly from the needle placement site.

In another aspect, the invention relates to a complete assembly for injection of anesthetic in the peribulbar region of the eye comprising a hub with a needle attached to one end and the other end dimensioned to receive the male end of a syringe, a pressure-directed flange attached to the hub and extending substantially perpendicular to the axis of the hub, and a syringe attached to the hub.

In yet another aspect the invention relates to a detachable pressure-directed flange which may be secured to a needle assembly.

BRIEF DESCRIPTION OF THE DRAWINGS

FIG. 1 is a perspective view of one embodiment of the invention comprising a tunnel portion on the flange.

FIG. 2 is a perspective view of an alternative embodiment of the invention comprising an open channel portion on the flange.

FIG. 3 is an elevation view of an alternative embodiment of FIG. 1, showing a vee-shaped flange.

FIG. 4 is elevation view of FIG. 1, illustrating dimensions.

FIG. 5 is an elevation view of an alternative embodiment.

FIG. 6 is a side view of the embodiment shown in FIG. 5.

FIG. 7 is a perspective view of the embodiment shown in FIG. 1 operatively attached to a syringe assembly.

FIG. 8 is a perspective view of the embodiment shown in FIG. 5 operatively attached to a syringe assembly.

DETAILED DESCRIPTION

Figure 9:
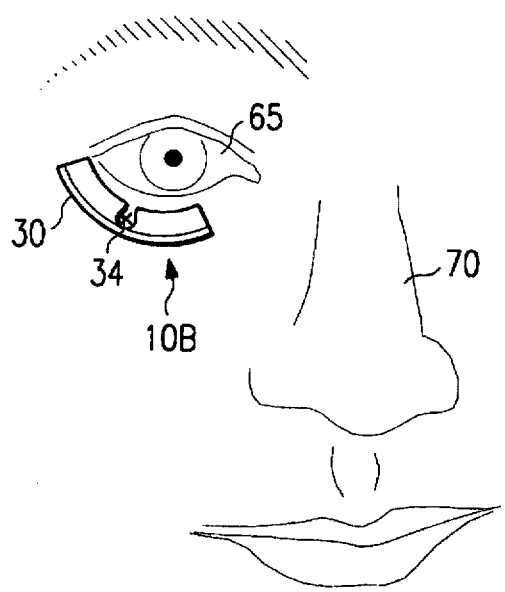
FIG. 9 is an elevation view of the flange member shown in FIG. 2 at a preferred site of application.

Although the pressure-directed peribulbar anesthesia delivery device may be satisfied by several embodiments and different forms, the device shown in the drawings and herein described is the preferred embodiment of the device and its application. The present disclosure is to be considered exemplary of the principles of the invention and is not intended to limit the invention to the embodiments herein illustrated.

Turning to the drawings, FIG. 1 illustrates a first embodiment of the pressure-directed peribulbar anesthesia delivery device. The device 5 includes a flange 10A secured to a needle assembly 12. The flange is of a shape and dimension to fit essentially adjacent the inferior orbital ridge when in use and to apply pressure to the area below the eye. As illustrated in FIG. 1, the flange 10A is in the semilunar shape, but other shapes including vee-shaped flange 10A as best illustrated in FIG. 3 may be used as long as pressure is applied adjacent the injection site as will be discussed in more detail below. The exact dimensions of the flange illustrated in FIGS. 1 and 4 as 10A, FIG. 2 as 10B, FIG. 3 as 10C and FIG. 5 as 10D may vary depending on the size of the patient. For example, dimensions are expected to vary for adults and children. FIGS. 1, 4 and 7 depicts a semilunar crescent-shaped flange. As best illustrated in FIG. 4, the length (l) of the semilunar flange for the average adult is from about 1.0 to about 1.5 inches from outer tip to outer tip; a length of about 1.3 to 1.5 inches has been found useful. Additionally, a height (h) rising from the ends of the flange to the apex of the crescent can be from about 0.4 to about 0.75 inch for the average adult. The width (w) of the flange can vary. FIG. 2 depicts flange 10B which is similar in shape to flange 10A of FIG. 1, but which has portions defining an open channel 34 designed to receive and hold needle assembly 12. Flange 10B is ideally comprised of sufficiently flexible material so that the open channel portion 34 can be temporarily flexed to receive needle assembly 12 and then released to securely hold needle assembly 12.

In the illustrated embodiments of FIGS. 1, 2, 3, 4 and 7, a surface 30 is provided to press against the patient in use, and a support portion 32 as best seen in FIGS. 1, 2 and 7 is provided as structure for attachment to the needle assembly 12 as well as for rigidity of the flange. However, other structures can be employed as long as the flange is made with a width sufficient to allow attachment to needle assembly 12 to provide sufficient rigidity to the overall device so that adequate pressure can be applied without collapse, and so that appropriate lateral pressure from the needle injection site is applied to the patient in use. The width need not be constant.

As best illustrated in FIG. 1, the illustrated semilunar-shaped flange 10A has a portion defining a tunnel 35. In one embodiment, the tunnel is defined in a location approximately central of flange 10A, but it may be located elsewhere as long as the portion of flange 10A, extending laterally from the needle injection site will not be impeded during use and adequate pressure is applied in the under eye region. FIG. 2 illustrates an alternative embodiment with a portion defining open channel 34, also illustrated with an essentially central area for receiving needle assembly 12. In accordance with a further aspect of the invention, FIGS. 5 and 8 illustrates a semilunar-shaped flange 10D having portions defining an aperture located near an end of the flange. The flange in FIG. 5, shown in cross section in FIG. 6, illustrates that the flange can be of any desired cross-sectional shape. The important factor is providing a surface such as surface 30 in FIGS. 1–4 and 7 and surface 31 in FIGS. 5 and 8 which will press against the patient in use. It should also be recognized that the embodiment shown in FIGS. 5 and 6 can be essentially hollow as depicted or can be made of solid material encasing needle assembly 12. The configurations shown in FIGS. 1 and 7 show support portion 32 which in use extends laterally outwardly from the needle hub ball 22. The flange can also be essentially oval or circular in cross-section thus providing a smooth surface 31 as shown in FIGS. 5, 6 and 8.

Referring again to FIG. 1, the needle assembly 12 includes a hub 20 and a hollow needle 15. The hub 20 of the needle assembly 12 is secured to the portions defining a tunnel 35 and is securely positioned through an appropriate securement means such as friction fit or adhesion as illustrated in FIG. 1. The portion defining a tunnel 35 may also be provided with other connection means, such as threads complementary to threads provided on a hub for connection between the two pieces. FIG. 2 shows an embodiment in which portions define a receiving area in the form of an open channel 34. The portion defining open channel 34 allows the flange 10B to flex so that when flexed, a needle hub 20 may be placed in the opening and when released, flange 10B will securely hold the needle hub 20 in the opening. Alternatively, the device illustrated in FIG. 1 need not have portions defining tunnel 35 but may be an integral embodiment. Hub 20 and flange 10A can be molded in one piece, thus eliminating the need for said tunnel 35 to be provided. Needle 15 can be attached to such an integrally molded combination hub/flange to form the operative assembly of the semilunar-shaped flange 10A.

Needle 15 can be of several lengths, the preferred lengths being from about ½ inch to about ¾ inch. Longer lengths can be used up to about one inch in length, although such longer lengths will not realize all the advantages of the invention since shorter lengths are less risky but still effective. A preferred needle gauge for eye block (anesthetic) procedures is 25 gauge, but any appropriate gauge can be used.

There are several plastic processing techniques available for manufacturing the invention, however, the preferred techniques originate in the art of molding. For the integral embodiment of the invention, a molding of the embodiment in FIG. 1 is designed. Any of the following plastic processing techniques can be used to form the integral embodiment: injection molding; rotational molding; blow molding; or stamping. Any plastic suitable for medical applications may be used such as those currently used for syringes. Other materials may also be used of a consistency which allows for appropriate pressure to be applied and stiffness. Such alternatives may include silicone, rubber, latex, glass and others. A carbon or stainless steel needle is attached by methods standard in the art to the complete the embodiment.

For the discrete embodiment of the invention, a molding of flanges 10A, 10B, 10C or 10D in FIGS. 1, 2, 3 or 5 is made. The preferred molding shape is proportional to the dimensions of a typical under-eye area found along the inferior orbital ridge. The shape and size can be adapted so that it will better fit persons of different eyes or other characteristics. In alternative embodiment 10C of FIG. 3, a vee-shaped embodiment is made having a receiving area for a needle assembly near the apex. The device may also be used for animal eye surgery and the size and shape adapted to fit particular animals. For non-human animals, it is expected the technique will be most useful for administration of drugs for post operative pain relief, since most, if not all, such animals are normally fully anesthetized by veterinarians prior to eye surgery. Any of the above plastic processing techniques can be used to form flange 10A, 10B, 10C or 10D. A commercially available needle assembly can be purchased and then attached to flange 10A, 10B, 10C or 10D with standard techniques and for needle to hub attachment to create a peribulbar device 5 ready for attachment to a syringe As best seen in FIGS. 1 and 2, the hub 20 of the needle assembly 12 includes a lumen 25 and two ends. The distal end or hub ball 22 of the hub 20 attaches to the needle 15. As best shown in FIGS. 7 and 8, the proximal end 23 extends to form a female adaptor which is connected in use to a male adaptor 38 of a syringe assembly 36.

A standard syringe is usable with the invention. FIGS. 7 and 8 illustrate a standard syringe. The syringe assembly 36 includes a plunger assembly 55, a male adaptor 38, and a barrel 40. The barrel 40 has a cylindrical portion 45 and a proximal portion 50. The cylindrical portion 45 receives the plunger assembly 55. So that the user of the invention can better administer the anesthesia, the proximal portion of the syringe assembly 50 preferably contains a finger flange 60.

In carrying out the application of the invention, the user attaches the pressure-directed peribulbar device 5 to a syringe assembly, such as syringe assembly 36, and draws a fluid to be fluid to be administered into the cylindrical portion 45 of the barrel 40.

Figure 10:
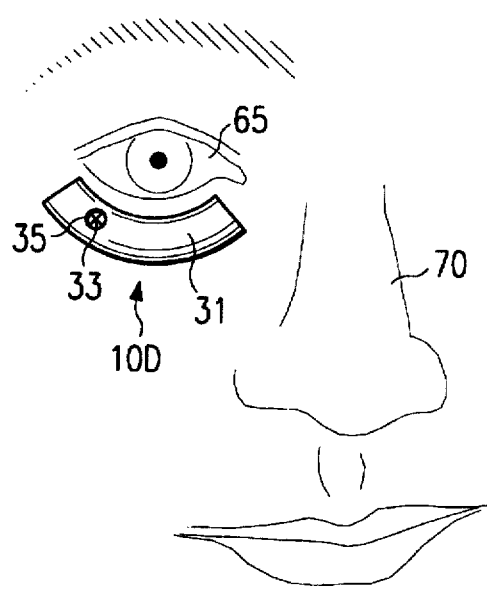
FIG. 10 is an elevation view of the flange member shown in FIG. 5 at a preferred site for the anatomical right eye.
Figure 11:
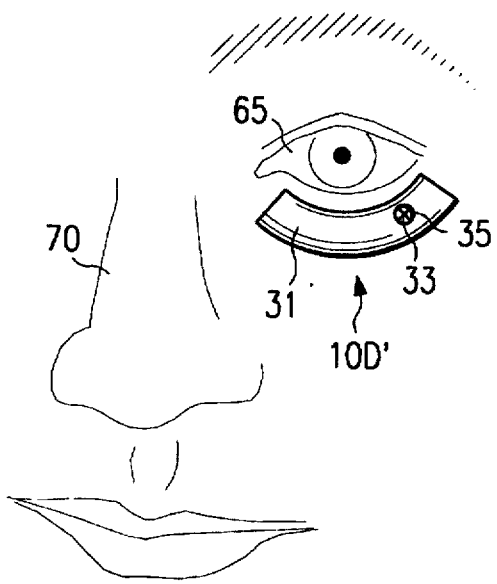
FIG. 11 is another aspect of the flange member shown in FIG. 5 at a preferred site for the anatomical left eye.

FIGS. 9–11 show the alternate embodiments of device 5 without the attached needle assembly to better demonstrate the preferred site of injection. The preferred site of injection shown by an "X" in the drawings is just above the inferior orbital ridge at the lateral limbus of the iris when the eye is in neutral gaze. FIG. 9 illustrates the preferred positioning of a flange 10B of FIG. 2 at the anatomical right eye located to the right of patients nose 70. This would be the same approximate positioning for flange 10A of FIG. 4. Shown in FIG. 9 is a portion defining an open channel 34 into which the hub of needle assembly 12 can be snapped and held in place. Flange 10B attaches to the hub of a needle assembly 12 by a snap-fit. Preferably the surface 30 of the flange is even with the needle hub ball 22 but it can be attached in any position allowing flange contact to exert pressure lateral from the needle injection site adjacent the inferior orbital ridge. FIGS. 10–11 illustrate the preferred positioning of the flange 10D shown in FIG. 5 for needle injection. FIG. 10 shows flange 10D adjacent the inferior orbital ridge of the anatomical right eye. FIG. 11 demonstrates the preferred positioning of flange 10D', the mirror image of 10D at the anatomical left eye. The user applies adequate pressure to insert needle 15 (not shown) at the selected site of injection shown by "X" in FIGS. 10 and 11.

Figure 12:
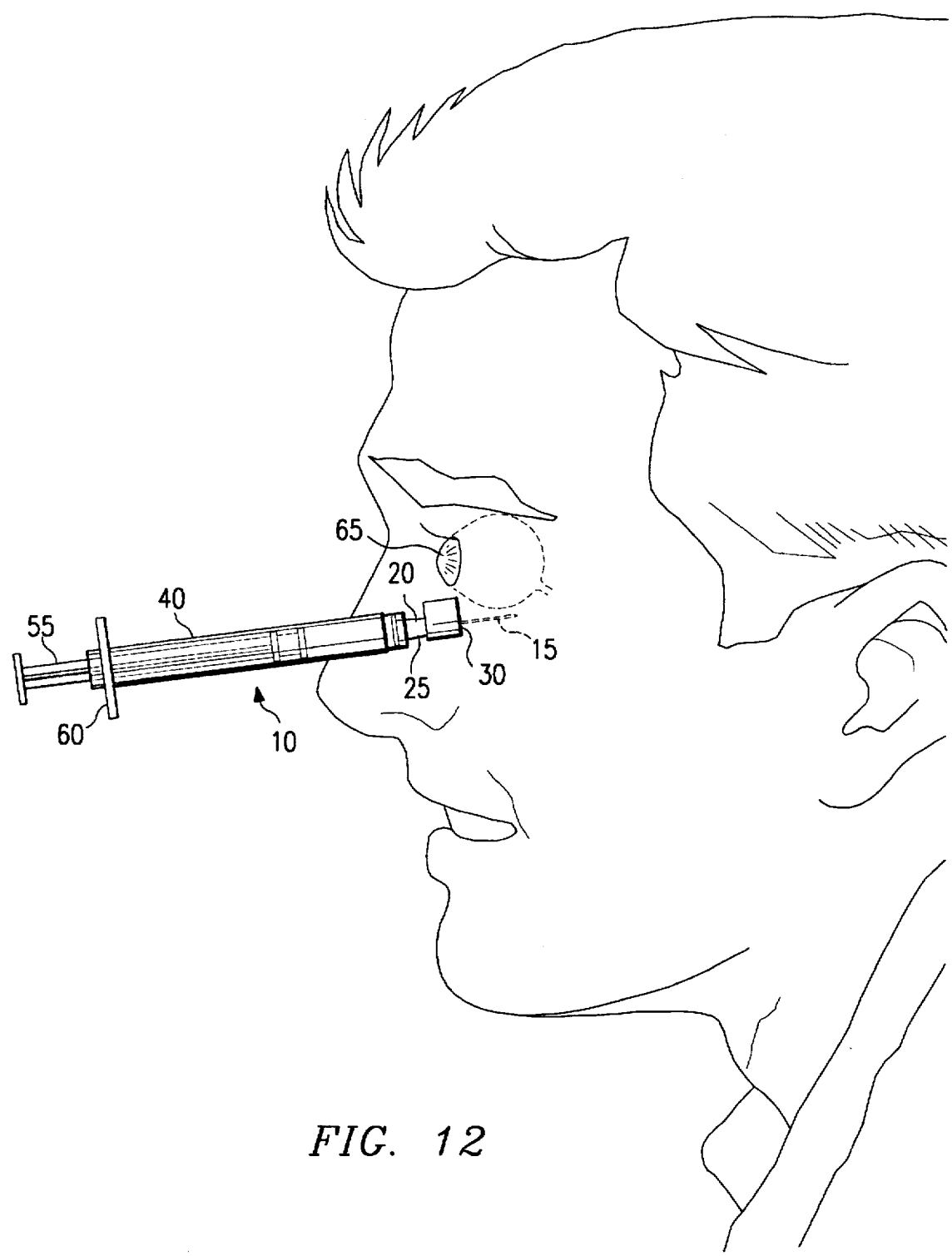
FIG. 12 is a side elevation view of the embodiment shown in FIG. 1 operatively attached to a syringe assembly and positioned at a preferred site of application.

Needle 15 upon insertion is located in the peribulbar region of the eye above the inferior orbital ridge as best presented in FIG. 12, such that the flange 10 rests along the inferior orbital ridge of the skull. The angle of entry is preferably tangential relative to the globe of the eye 65; gradually pronated to a final position of perpendicular relative to the skin when fully inserted ½ to ¾ inch under the skin. Another technique can be used with the device of the invention in which the needle penetrates perpendicular to the skin ½ to ¾ inch with pressure applied on injection. It has been found that no pronation or turning of needle toward the eyeball is necessary for an effective block. After a negative blood aspiration of syringe is made, pressure on the semilunar-shaped flange 10 is exerted while injecting local anesthetic below the eye along the inferior orbital ridge. This pressure directs the anesthetic into the peribulbar space thus visibly causing the eyeball to bulge forward. This position allows surgery to be facilitated. The fluid is distributed throughout the peribulbar region by using the forces applied by the apparatus of the invention.

The method and apparatus of the pressure-directed anesthesia delivery device, thus allows anesthesia to be effectively distributed throughout the peribulbar region of the eye, e.g. peribulbar space, after a single administration. The device enables the practitioner to apply the necessary pressure along the inferior orbital ridge, closest to the injection site, while concomitantly stabilizing the needle so the anesthetic is properly injected into the peribulbar region with less extravasation into the surrounding tissue. Moreover, the pressure-directed anesthesia delivery device provides greater safety for the recipient of the anesthesia since the user can apply a shorter needle and use a lesser quantity of drug. It has been found, for example, that a typical dosage of 10 cc of local anesthesia comprising 4.5 cc bupivacaine 0.75% (MPF), 4.5 cc lidocaine 2% (MPF) and 1 cc hyaluronidase 150 USP units, can be reduced substantially. See Examples 1 and 2. Using a smaller needle reduces the incidence of inadvertently perforating the globe of the eye or causing a retrobulbar hemorrhage. A lower dose of anesthetic provides several benefits. First, it is safer for the patient in the sense that potential harm from side-effects of the anesthesia dissipates, especially for glaucoma patients having variable intraocular pressures. Additionally, patients who receive a lower dose of anesthesia recover more rapidly. Post-operatively, such patients have a clearer appearing eye without redness and ecchymosis. Thirdly, there is an economic benefit for using a lower dose of drug which the practitioner, hospital and/or patient receives.

The pressure-directed anesthesia delivery device provides benefits of effective drug delivery in the peribulbar region, reduced risk of injury by permitting effective use of shorter needles and permits less drug to be used. It can be made either as a flange which can be secured permanently or detachably attached to the hub of a standard hypodermic needle, or as a flange assembly with an integral hub and preferably a needle attached thereto. The device is preferably pre-sterilized, and ready to receive a syringe without further assembly. It is also envisioned that preferably the device will be disposable to permit it to meet standards in place for use and disposal of needles and syringes.

EXAMPLE 1

A patient with a history of glaucoma and low intraocular pressure (0 mm Hg) secondary to leaking bleb was prepared for surgery with a peribulbar block. The anesthesia was administered to the patient using the pressure-directed anesthesia delivery device as shown in FIG. 1. The objective of a good peribulbar block was achieved with a three cc dose of a local anesthetic containing 1 cc bupivacaine 0.75% (MPF) methyl paraben free, 1 cc lidocaine 2% (MPF), and 1 cc hyaluronidase 150 USP units. According to experience, using prior techniques, up to 6–10 cc of anesthesia, were usually required in order to meet the objective of adequate anesthesia for the operation. It was desirable for this particular patient to limit the amount of volume because the more the volume in the peribulbar space, the greater the risk of globe compression and possible retinal detachment or vitreous hemorrhage. The use of the invention provided a beneficial effect and a lowering of the risk to this patient.

EXAMPLE 2

A patient was prepared for a cataract extraction with an intraocular lens implant, using a clear cornea technique. Anesthesia was administered using the pressure-directed anesthesia delivery device shown in FIG. 1 of 3.5 cc of the following composition: 1.25 cc bupivacaine 0.5% (MPF) with 1:200,000 of epinephrine, 1.25 cc lidocaine 2% (MPF), and 1 cc hyaluronidase 150 USP units. It was found that the area of the cornea through which the surgical incision was made remained flat and clear facilitating the surgeon's operation and aesthetically pleasing without redness and swelling of the conjunctiva. Without the use of the invention, 6–10 cc of anesthesia were often required and on occasion supplements (additional doses of anesthesia) were required to achieve the aesthetic effect desired. With this particular patient, the use of the invention provided benefits as described and the ability to lower the volume of the anesthetic, beneficial to the patient and the surgeon. Larger volumes of anesthetic tend to flow forward causing chemosis and interference with the surgical field.

EXAMPLE 3

Administers of anesthesia in the form of peribulbar blocks were observed empirically by comparing the success rate using standard techniques as compared to use of the pressure-directed anesthesia delivery device of the invention. It was observed that among professionals with no previous experience in administering eye blocks, the success rate improved from approximately 50% to 98% or better. It is further observed that lower volumes of anesthesia were required and less complications arose. It is further observed that less repetition of blocks, i.e., less supplements of anesthesia, were required to be administered because of the improvement in delivery facilitated by the invention.

We claim:

1. A device for delivering peribulbar anesthesia comprising:

a) a syringe assembly comprising:
   a needle hub including a proximal end, a distal end, and first threaded connector means therebetween;
   a hollow needle having a length of 0.5 to 0.75 inches attached to the distal end of said needle hub; and
   a syringe barrel including a plunger assembly attached to the proximal end of said needle hub; and b) a flange releasably attached to said syringe assembly comprising:
   a semi-circular skin-contacting side including means for transmitting sufficient pressure to space between the inferior orbital ridge and the lower eyelid of a patient to prevent the deposit of anesthetic throughout tissue in said space;
   a semi-circular syringe-receiving side; and
   a portion defining a tunnel between said skin-contacting side and said syringe-receiving side, said portion including second threaded connector means for engaging said first threaded connector means,
   wherein said proximal end of said needle hub is located proximal of said syringe-receiving side and said distal end of said needle hub is located proximal of said skin-contacting side.

2. A method of delivering peribulbar anesthesia to a patient comprising the steps of:

a) providing a device for delivering pefibulbar anesthesia comprising:
   i) a syringe assembly comprising:
      a needle hub including a proximal end, a distal end, and first threaded connector means therebetween;
      a hollow needle having a length of 0.5 to 0.75 inches attached to the distal end of said needle hub; and
      a syringe barrel including a plunger assembly attached to the proximal end of said needle hub; and
   ii) a flange releasably attached to said syringe assembly comprising:
      a semi-circular skin-contacting side including means for transmitting sufficient pressure to space between the inferior orbital ridge and the lower eyelid of a patient to prevent the deposit of anesthetic throughout tissue in said space;
      a semi-circular syringe-receiving side; and
      a portion defining a tunnel between said skin-contacting side and said syringe-receiving side, said portion including second threaded connector means for engaging said first threaded connector means,
      wherein said proximal end of said needle hub is located proximal of said syringe-receiving side and said distal end of said needle hub is located proximal of said skin-contacting side; and b) injecting anesthetic into the peribulbar region of a patient while simultaneously applying pressure to space between the inferior orbital ridge and lower eyelid of said patient to prevent the deposit of anesthetic throughout tissue located in said space.

* * * * *